United States Patent
House

(10) Patent No.: US 11,883,611 B2
(45) Date of Patent: Jan. 30, 2024

(54) CATHETER SYSTEM WITH LINEAR ACTUATION CONTROL MECHANISM

(71) Applicant: Edwards Lifesciences Corporation, Irvine, CA (US)

(72) Inventor: Morgan House, Newfields, NH (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 216 days.

(21) Appl. No.: 17/359,450

(22) Filed: Jun. 25, 2021

(65) Prior Publication Data

US 2021/0322726 A1    Oct. 21, 2021

Related U.S. Application Data

(63) Continuation of application No. 15/956,395, filed on Apr. 18, 2018, now Pat. No. 11,045,627.

(60) Provisional application No. 62/486,956, filed on Apr. 18, 2017.

(51) Int. Cl.
*A61M 25/01* (2006.01)
*A61M 25/09* (2006.01)

(52) U.S. Cl.
CPC .... *A61M 25/0147* (2013.01); *A61M 25/0136* (2013.01); *A61M 2025/015* (2013.01); *A61M 2025/09116* (2013.01)

(58) Field of Classification Search
CPC .......... A61M 25/0133; A61M 25/0147; A61M 25/0105; A61M 25/0136; A61M 2025/0161; A61M 2025/015; A61M 2025/09116; A61F 2/2427
USPC .......................................................... 604/95
See application file for complete search history.

(56) References Cited

U.S. PATENT DOCUMENTS

| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |

(Continued)

FOREIGN PATENT DOCUMENTS

| CN | 102869318 A | 1/2013 |
| CN | 113331995 A | 9/2021 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Theodore J Stigell
*Assistant Examiner* — Nidah Hussain
(74) *Attorney, Agent, or Firm* — Anya Adams

(57) ABSTRACT

A handle shaft is disposed at a proximal end of a catheter. A wire extends from a distal part of the catheter, proximally through the catheter to the handle shaft. A knob is disposed outside of the handle shaft. A threaded mechanism provides operative coupling between the knob and the handle shaft such that (i) rotation of the knob with respect to the handle shaft alters tension in the wire via the threaded mechanism functioning as a linear actuator; and (ii) non-rotational axial movement of the knob with respect to the handle shaft alters tension in the wire without the threaded mechanism functioning as a linear actuator. Other embodiments are also described.

15 Claims, 10 Drawing Sheets

(56) References Cited

U.S. PATENT DOCUMENTS

| | | |
|---|---|---|
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,332,402 A | 7/1994 | Teitelbaum |
| 5,346,498 A | 9/1994 | Greelis et al. |
| 5,364,408 A | 11/1994 | Gordon |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,733,331 A | 3/1998 | Peredo |
| 5,749,371 A | 5/1998 | Zadini et al. |
| 5,752,963 A | 5/1998 | Allard et al. |
| 5,782,844 A | 7/1998 | Yoon et al. |
| 5,810,746 A | 9/1998 | Goldstein et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,048,351 A | 4/2000 | Gordon et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |

(56) References Cited

U.S. PATENT DOCUMENTS

| | | |
|---|---|---|
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,431,726 B2 | 10/2008 | Spence et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,029,556 B2 | 10/2011 | Rowe |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |

(56) References Cited

U.S. PATENT DOCUMENTS

| | | |
|---|---|---|
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0107531 A1 | 8/2002 | Schreck et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |

(56) References Cited

U.S. PATENT DOCUMENTS

| | | |
|---|---|---|
| 2004/0148021 A1 | 7/2004 | Cartledge et al. |
| 2004/0162610 A1 | 8/2004 | Liska et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0267571 A1 | 12/2005 | Spence et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0010857 A1 | 1/2007 | Sugimoto et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086164 A1 | 4/2008 | Rowe |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |

(56) References Cited

U.S. PATENT DOCUMENTS

| | | |
|---|---|---|
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076547 A1 | 3/2009 | Sugimoto et al. |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093670 A1 | 4/2009 | Annest et al. |
| 2009/0093877 A1 | 4/2009 | Keldar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissi |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0292353 A1 | 11/2009 | Yoganathan et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | Van Der Burg et al. |
| 2010/0063550 A1 | 3/2010 | Felix et al. |
| 2010/0063586 A1 | 3/2010 | Hasenkam et al. |
| 2010/0070028 A1 | 3/2010 | Sugimoto |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0210899 A1 | 8/2010 | Schankereli |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0292785 A1 | 11/2010 | Seguin et al. |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0015476 A1 | 1/2011 | Franco |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0184510 A1 | 7/2011 | Maisano et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0029627 A1 | 2/2012 | Salahieh et al. |
| 2012/0035712 A1 | 2/2012 | Maisano et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0203336 A1 | 8/2012 | Annest |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0310840 A1 | 12/2012 | Colombo et al. |
| 2012/0323313 A1 | 12/2012 | Seguin |
| 2013/0018459 A1 | 1/2013 | Maisano et al. |
| 2013/0030522 A1 | 1/2013 | Rowe et al. |
| 2013/0046373 A1 | 2/2013 | Cartledge et al. |

(56) References Cited

U.S. PATENT DOCUMENTS

| | | |
|---|---|---|
| 2013/0046380 A1 | 2/2013 | Maisano et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0350662 A1 | 11/2014 | Vaturi |
| 2014/0379006 A1 | 12/2014 | Sutherland et al. |
| 2015/0018940 A1 | 1/2015 | Quill et al. |
| 2015/0025553 A1 | 1/2015 | Del Nido et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112429 A1 | 4/2015 | Khairkhahan et al. |
| 2015/0112432 A1 | 4/2015 | Reich et al. |
| 2015/0119936 A1 | 4/2015 | Gilmore et al. |
| 2015/0119979 A1 | 4/2015 | Maisano et al. |
| 2015/0127097 A1 | 5/2015 | Neumann et al. |
| 2015/0133997 A1 | 5/2015 | Deitch et al. |
| 2015/0164637 A1 | 6/2015 | Khairkhahan et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0089126 A1* | 3/2016 | Guo ................ A61M 25/0147 604/95.04 |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0206853 A1* | 7/2016 | Bolduc ............ A61M 25/0136 |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0098821 A1* | 4/2018 | Saul ........................ A61B 8/56 |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 1034753 A1 | 9/2000 |
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2008112740 A2 | 9/2008 |
| WO | 2010000454 A1 | 1/2010 |
| WO | 2012004679 A2 | 1/2012 |
| WO | 2012178115 A2 | 12/2012 |

(56) References Cited

FOREIGN PATENT DOCUMENTS

| | | |
|---|---|---|
| WO | 2012176195 A3 | 3/2013 |
| WO | 2014064964 A1 | 5/2014 |
| WO | 2014134183 A1 | 9/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, All et al. "Percutaneously adjustable pulmonary artery band." The Annals of thoracic surgery 60 (1995): S520-S522.
Alfieri et al. "Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischernic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

CATHETER SYSTEM WITH LINEAR ACTUATION CONTROL MECHANISM

CROSS-REFERENCE TO RELATED PATENT APPLICATIONS

This application is a Continuation of U.S. Ser. No. 15/956,395 to House et al., filed Apr. 18, 2018, which is based on and claims priority to U.S. Provisional Patent Application 62/486,956, filed Apr. 18, 2017. Each of the above applications is incorporated by reference herein as if expressly set forth in its respective entirety herein.

TECHNICAL FIELD

The present teachings generally relate to a delivery catheter with a deflectable distal portion. In one aspect, the delivery catheter can include a control mechanism for precisely controlling the deflecting angle of the distal portion of the delivery catheter.

BACKGROUND

Deflectable catheters usually feature a tip that can be pulled into a defined curve. This deflection of the catheter tip is independent of the rest of the catheter. Such movement can be achieved by exerting a force biased to one side of the distal portion by using a wire connected to a pull or anchor ring near the tip. The catheter tip can return to its original shape when the force is reduced or removed.

Deflectable catheters have been used in cardiology, peripheral vascular therapies, structural heart therapies, and many other fields that require the catheter tip to make angulated turns or to be fairly accurately positioned in an anatomy. Examples include guiding catheters, implant delivery systems, or EP mapping catheters, and ablation catheters.

The deflectable catheters in the market include uni-directional catheter, bi-directional catheters, 4-way deflectable catheters, and omni-directional catheters. A bi-directional catheter features a tip that can be pulled in two directions (often opposite from each other). This can be achieved by using two pull wires connected to a distal pull ring. A 4-way deflectable catheter can be pulled in 4 directions. The 4-way deflectable catheter often requires four wires connected to a distal pull ring. An omni-directional catheter is a 4-way deflectable catheter that is often remotely controlled by a robotic device to allow the tip to be deflected in any direction. Deflection is achieved by manipulating one or more of the pull wires simultaneously. Robotic catheters can be used for a variety of applications and provide the physician with a greater control and less exposure to radiation.

The deflectability of the catheter tip can be qualified in many ways. A "curve angle" is measured as the angle of the tip movement relative to its straight axis, i.e. the bend angle. The term "bend radius" refers to the inside curvature of the catheter and indicates the minimum radius one can bend a catheter without kinking it. Most deflectable catheters have a curve angle ranging between about 45 and about 180 degrees depending on the application, but can be up to about 270 degrees or in some instances 360 degrees. A "curve diameter" indicates the furthest distance that the catheter moves from its straight axis as it is being deflected. The "reach" measures the displacement of the tip from its central or straight axis.

Deflectable catheters also are categorized as single plane deflection catheters and bi-plane deflection catheters. A single plane deflection catheter deflects within a single plane and includes all uni-directional catheters and most bi-directional catheters. The tip of a bi-plane deflection catheter can deflect along X and Y axis. In other words, it turns side to side and forwards or backwards. Bi-plane deflection catheters include 4-way deflectable catheters.

The deflection of the catheter tip is typically achieved by one or more pull wires via a control mechanism. The most common control mechanism is a simple push-pull mechanism that extends or retracts the pull wire and thereby actuates the deflection of the catheter tip. Thus, the relative linear motion of the push-pull mechanism decides the bend angle and control the planarity of the catheter tip. Although easy to operate, the linear motion of the push/pull mechanism lacks the ability to precisely control the bend angle. In percutaneous applications, the curve angle of a deflectable tip needs to be able to be meticulously adjusted in order for a clinician to find a desired location inside each individual anatomy. Thus, the lack of the ability to be finely adjusted must be improved to allow a clinician to better treat patients.

SUMMARY

One aspect of the present teachings provides a catheter assembly that comprises a catheter shaft and a control mechanism. The catheter shaft has a deflectable distal portion. The control mechanism is configured to activate a rapid transformation of the deflectable distal portion of the catheter shaft from a linear profile to a curved profile. The control mechanism further comprises a linear actuation mechanism. The linear actuation mechanism converts a rotation motion of the control mechanism to a precise linear motion. The linear motion of the control mechanism is configured to control the bend angle of the deflectable distal portion of the catheter shaft.

Another aspect of the present teachings provides a catheter assembly that comprises a catheter shaft, a pull wire joining the distal end of the catheter shaft, and a control mechanism. The pull wire is configured to deflect a distal portion of the catheter shaft. The control mechanism includes a compression tube mount, and a pull wire mount. A proximal portion of the catheter shaft joins the compression tube mount. A proximal end of the pull wire joins the pull wire mount. A change in distance between the pull wire mount and the compression tube mount results the deflection of the distal portion of the catheter shaft.

Another aspect of the present teachings provides a control mechanism comprising an outer handle shaft, a middle handle shaft. The middle handle shaft is positioned inside an interior lumen of the outer handle shaft. The middle handle shaft has a first position wherein the middle handle shaft engages an interior surface of the outer handle shaft via a thread engagement, and a second position wherein the middle handle moves laterally without the restriction of the thread engagement.

Another aspect of the present teachings provides a control mechanism having a linear actuator. The linear actuator comprises a threaded rotator and a thread follower with pairing threads. The linear actuator is configured to convert the rotational motion of the threads into a relative linear motion of the middle handle and the outer handle shaft.

Another aspect of the present teachings provides a control assembly having the middle handle shaft automatically centers within the outer handle shaft by two centering springs. Each centering spring is placed on each side of the middle handle shaft. When the centering spring is in its relaxed state, the middle handle shaft in centered within the interior lumen of the outer handle shaft.

Another aspect of the present teachings provides the middle handle shaft having a thread engagement mechanism. The thread engagement mechanism comprises a thread follower that engages a thread inside the interior luminal surface of the outer handle shaft. The thread engagement mechanism further comprises a spring. When the spring is compressed, the thread follower engages the thread inside the interior luminal surface of the outer handle shaft. When the spring relaxes, the thread follower disengages from the threads inside the interior luminal surface of the outer handle shaft.

Another aspect of the present teachings provides a catheter assembly that comprises a catheter shaft and a control mechanism. The catheter shaft comprises a first configuration where a distal portion aligns with the longitudinal axis of the catheter shaft, and a second configuration where the distal portion curves away from the longitudinal axis of the catheter shaft.

DETAILED DESCRIPTION OF CERTAIN EMBODIMENTS

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction relatively away from a catheter insertion location and "proximal" refers to the direction relatively close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and appended claims are approximations. At the very least and not as an attempt to limit the application of the doctrine of equivalents to the scope of the claims, numerical parameters should be read in light of the number of reported significant digits and the application of ordinary rounding techniques.

The present teachings relate to an implant delivery catheter with a deflectable catheter tip, an ablation catheter with a deflectable tip or any therapy catheter requiring actuation at the distal section or tip. In some embodiments, the delivery catheter includes a control mechanism. In some embodiments, the control mechanism is a precision control mechanism. In certain embodiments, the control mechanism allows a clinician to control, sometimes accurately, the bend angle, reach and curve diameter of the deflectable tip.

Figure 1:
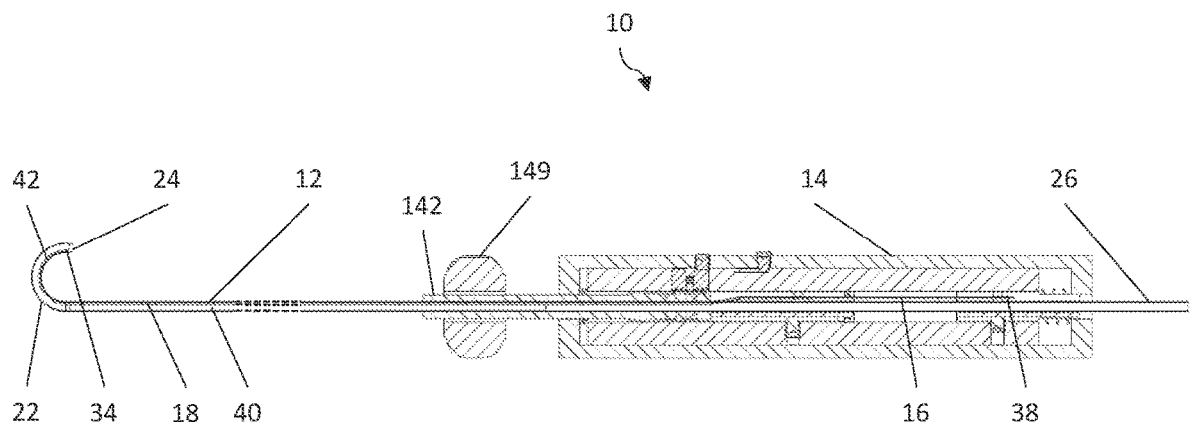
FIG. 1 is a perspective view of an embodiment of the present teachings where a delivery catheter assembly including a control handle assembly and a catheter shaft with a deflectable distal portion.

Referring now to FIG. 1, according to one embodiment of the present teachings, the delivery catheter assembly (10) includes a catheter shaft (12) having a distal portion (22), where the distal portion of the catheter shaft (12) is deflectable, and a control handle assembly (14) disposed at the proximal portion (26) of the catheter shaft (12). In some embodiments, the control handle assembly (14) is connected with the proximal portion (26) of the catheter shaft (12). In some embodiments, the control handle assembly (14) includes a pull wire (16). In some embodiments, the pull wire (16) extends along the longitudinal axis of the catheter shaft (12). In some embodiments, the pull wire (16) connects its distal end (34) to the distal end (24) of the catheter shaft (12) and connects the control handle assembly (14) at the proximal end (38). In some embodiments, when a clinician applies tension on the proximal end (38) of a pull wire (16), such tension is transferred to the distal end (34) of the pull wire (16) and through the distal end (34) of the pull wire (16) that is connected with the distal end (24) of the catheter shaft (12). As a result, the catheter shaft (12) articulates in a single direction. In some embodiment, the pull wire (16) is positioned inside a peripheral lumen (18) extending along the catheter shaft (12). In some embodiments, the direction of the articulation is defined by the positions of the pull wire (16), or the peripheral lumen (18) that housing the pull wire (16), in reference to the center axis of the catheter shaft (12).

According to some embodiments, a catheter shaft (12) of the present teachings include a longitudinal axis that runs from its proximal end (28) to its distal end (24). In some embodiments, the catheter shaft (12) includes a central longitudinal lumen (40). In some embodiments, the central longitudinal lumen (40) allows an implant, including a RF wire or other devices, to slide through. In some embodiments, the catheter shaft (12) includes an elongated and generally flexible portion (42) and an articulable distal portion (22). In some embodiments, the articulable distal portion (22) is configured to bend, curve, or otherwise change its shape and position. In some embodiments, the articulation of the distal portion (22) is triggered by the control handle assembly (14).

Figure 2A:
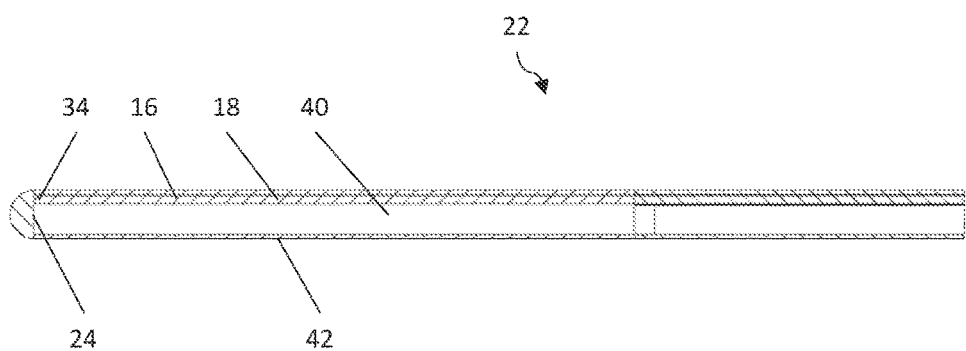
FIGS. 2A-2B are perspective views of a distal portion of the catheter shaft, according to one embodiment of the present teaching.
Figure 2B:
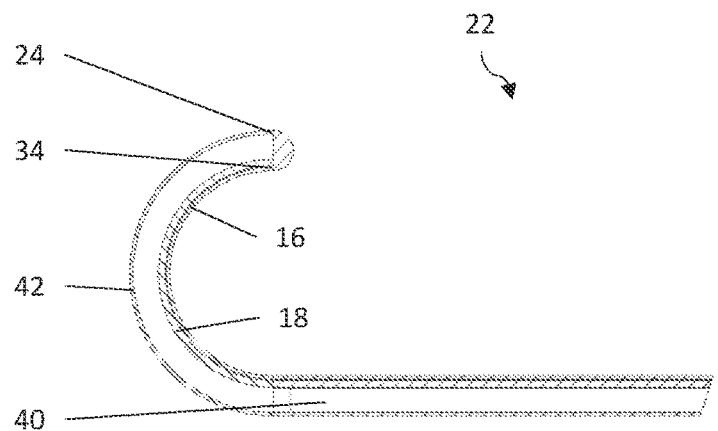

FIGS. 2A-2B illustrate one embodiment of the articulable distal portion (22). As shown in FIG. 2A, the pull wire (16) runs inside a peripheral lumen (18) exterior to the central longitudinal lumen (40) of the catheter shaft (12) along the length of the articulable distal portion (22) of the catheter shaft (12). The pull wire (16) attaches to the distal end (24) of the catheter shaft (12) by an attaching means. In some embodiments, the attaching means is a ring at the distal tip of the catheter shaft (12) to which the pull wire (16) is soldered. In some embodiments, the attaching means includes the pull wire (16) being embedded in the composite plastic or polymer material at the tip of the catheter shaft (12). In some embodiments, the pull wire (16) embedded in a composite of plastic or polymer are coiled at the attaching location, for example, to provide a strong attachment and to prevent the pull wire (16) from being pulled out of the composite material when tension is applied. As the tension is applied to the pull wire (16), the distal portion (22) of the catheter shaft (12) articulates in a single direction as shown in FIG. 2B.

According to some embodiments of the present teachings, both the generally flexible portion (42) and an articulable distal portion (22) of the catheter shaft (12) have a bending stiffness that allows the catheter (12) to be trans-luminally positioned through a tortuous path into the heart. According to some embodiments of the present teachings, the bending stiffness of the articulable distal portion (22) of the delivery catheter (12) is substantially less than the generally flexible portion (42) of the catheter shaft (12). In some embodiments, the catheter shaft (12) has sufficient column strength to remain substantially un-deflected when the pull wire (16) is tensioned. In some embodiments, the articulable distal portion (22) of the delivery catheter (12) is sufficiently flexible for deflection into a curvature.

In some embodiments, a middle portion (35) of the pull wire (16) is disposed within a peripheral lumen (18) unattached to the catheter shaft (12). The proximal end (38) of the pull wire (16) can be attached to the control handle assembly (14) as shown in FIG. 1. A proximal portion (26) of the catheter shaft (12) can be connected to the control handle assembly (14). According to one embodiment of the present teachings, the control handle assembly (14) is configured to apply an axial motion to manipulate the pull wire (16). In some embodiments, the manipulation of the pull wire (16) results in deflecting the distal portion (22) of the catheter shaft (12).

Figure 2C:
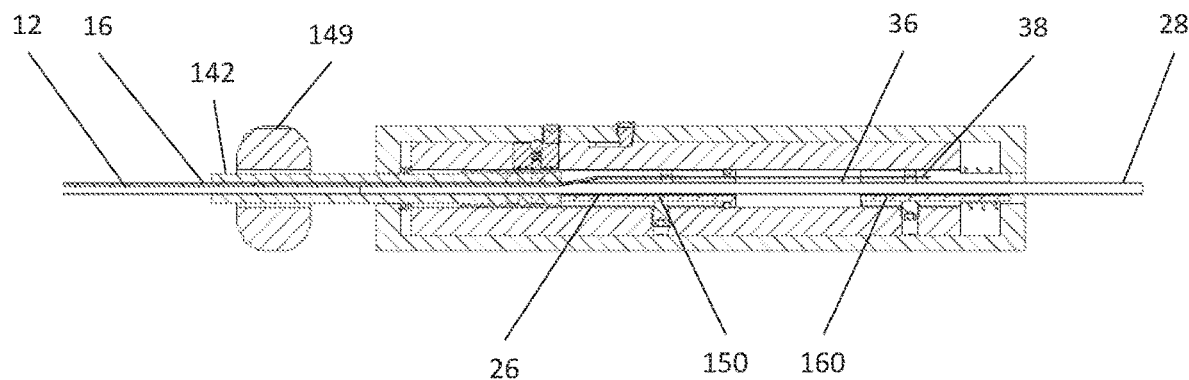
FIG. 2C is a perspective view of a control handle assembly, according to one embodiment of the present teaching.

FIG. 2C illustrates the proximal end portion (36) of the pull wire (16) and the catheter shaft (12). As shown in FIG. 2C, the proximal end (38) of the pull wire (16) is fixed to a pull wire mount (160). The proximal portion (26) of the catheter shaft (12) is fixed to a compression tube mount (150). The proximal end (28) of the catheter shaft (12) further extends proximally beyond the control handle assembly (14). The relative movement of the compression tube mount (150) and pull wire mount (160) will be translated to a relative motion between the catheter shaft (12) and pull wire (16), and thereby deflects the distal portion (22) of the catheter shaft (12).

Figure 3A:
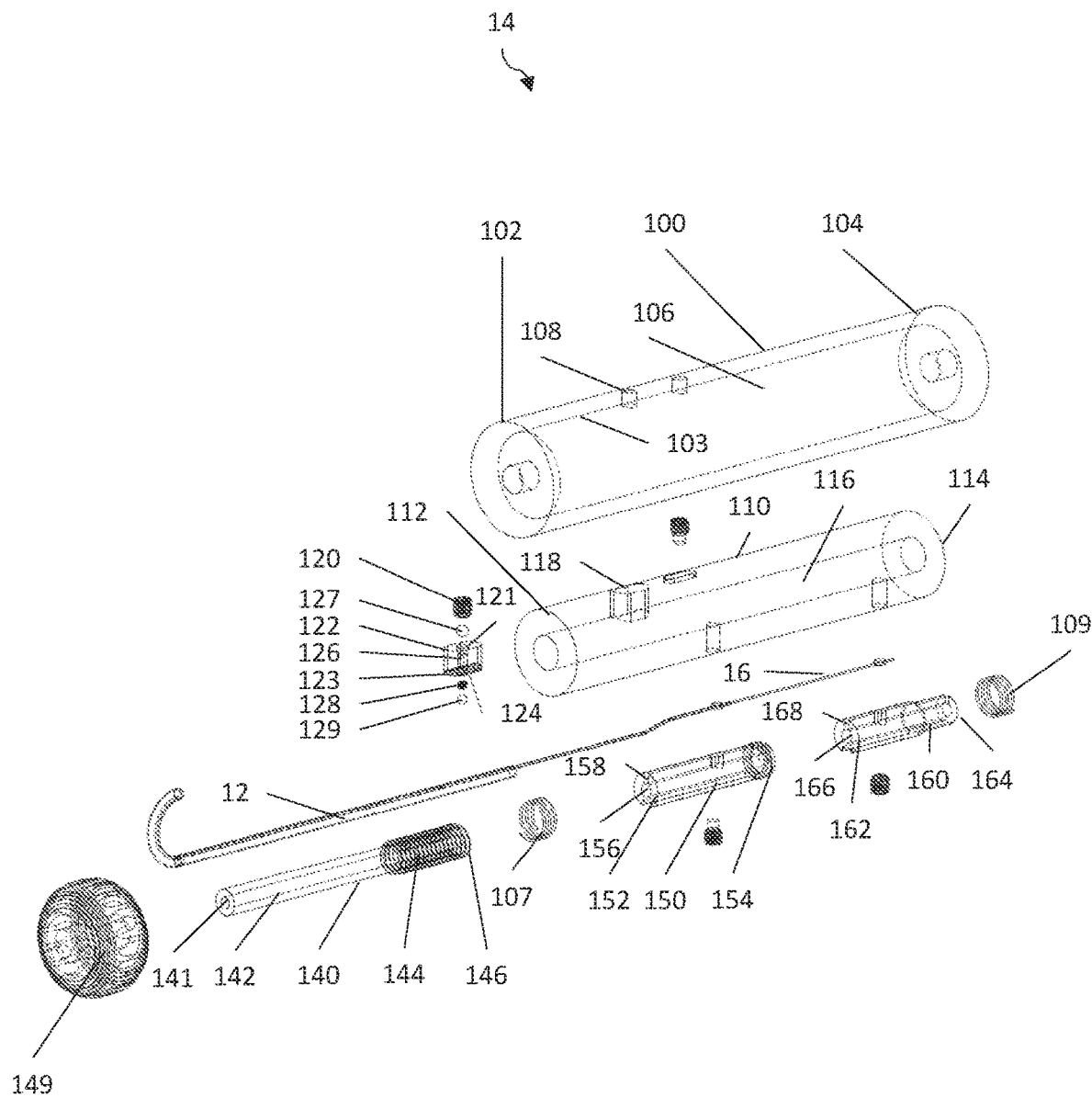
FIGS. 3A-3D are perspective views of a control handle assembly, according to one embodiment of the present teaching.
Figure 3B:
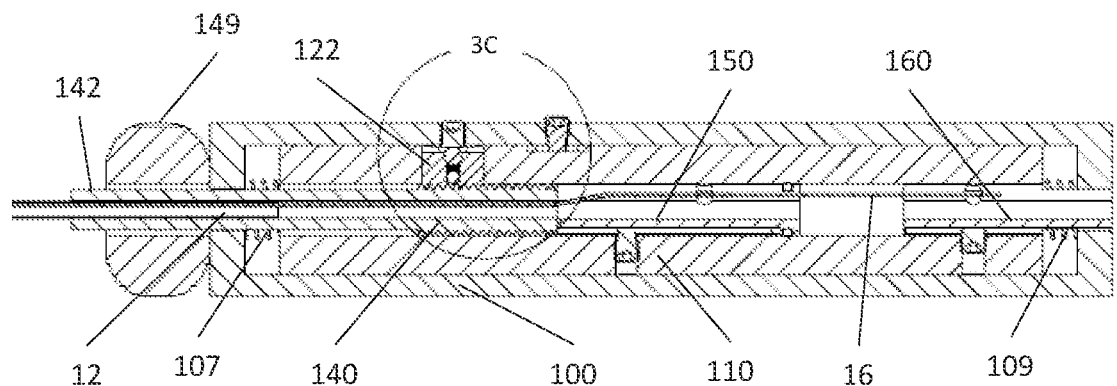

FIG. 3A illustrates an exploded view of the control handle assembly (14). FIG. 3B illustrates an assembled view of the control handle assembly (14). Now referring FIG. 3A, the control handle assembly (14) includes an elongated hollow outer handle shaft (100). In some embodiments, a hollow middle handle shaft (110) is disposed within the elongated hollow outer handle shaft (100). The distal end (102) of the outer handle shaft (100) is sized to allow a threaded rotator (140) to extend through, while block the middle handle shaft (110) in the outer handle shaft (100) from sliding proximally out. The proximal end (104) of the outer handle shaft (100) is sized to allow a catheter shaft (12) to extend through, while also blocking the middle handle shaft (110) from sliding distally out. The outer handle shaft (100) further has a center lumen (106) and a through hole (108) that extends from the center lumen (106) radially to the exterior surface (101) of the outer handle shaft (100). In some embodiments, the size of the through hole (108) is configured to house a set screw (120). In some embodiments, the location of the through hole (108) could vary along the outer handle shaft (100), so long as it centers over the thread follower (122) when the middle handle shaft (110) centers within the outer handle shaft (100). In some embodiments, a longitudinal slot is designed to allow a first ball bearing (127) to slide within. According to this embodiment, the longitudinal slot is placed on the interior surface (103) of the center lumen (106) starts near the through hole (108) and extends distally to the distal end (102) of the outer handle shaft (100).

FIG. 3A further illustrates an elongated middle handle shaft (110) having a center lumen (116) extending from its distal end (112) to its proximal end (114). The middle handle shaft (110) further includes a thread follower retainer slot (118). Similar to the through hole (108), the placement of the thread follower retainer slot (118) could vary so long as it allows the thread follower (122) centers under the set screw (120) when the middle handle shaft (110) centers within the outer handle shaft (100). The thread follower retainer slot (118) is designed to receive a thread follower (122). The center lumen (116) of the middle handle shaft (110) is sized to receive a threaded rotator (140), a compression tube mount (150), and a pull wire mount (160).

Continue referring to FIG. 3A, the thread follower (122) has a top side (121) and a bottom side (123). The bottom side (123) of the thread follower (122) has threads (124) configured to match the threads (144) of the threaded rotator (140). The thread follower (122) further includes a hole (126) for holding a first ball bearing (127) followed by a spring (128) in the middle and a second ball bearing (129). In some embodiment, the all ball bearings (127, 129) and the spring (128) are sized to be housed inside the hole (126), while the spring (128) is trapped in between the two ball bearings (127, 129) as shown in FIG. 3B. In some embodiment, when the middle handle shaft (110) is centered inside the outer handle shaft (100), the first ball bearing (127) is then resume its position and engages under the set screw (120). The set screw (120) then compresses the first ball bearing (127) downward. The first ball bearing (127) in turn compresses the spring (128) and thereby also pushes the thread follower (122) downward. In another embodiment, as the first ball bearing (127) moves away from its position under the set screw (120), the spring (128) relaxes and thereby allows the thread follower (122) moving upward.

Continue referring to FIG. 3A, a threaded rotator (140), a compression tube mount (150), and a pull wire mount (160) are placed inside the center lumen (116) of the middle handle shaft (110). In some embodiments, the threaded rotator (140), the compression tube mount (150), and the pull wire mount (160) are arranged from the distal end (112) to the proximal end (114) of the middle handle shaft (110). In some embodiments, the threaded rotator (140) has an elongated hollow body with a threaded proximal portion (144) and an unthreaded distal portion (142). As shown in FIG. 3A, the distal portion (142) extends from inside the middle handle shaft (110) and outer handle shaft (100) distally to the outside. In some embodiments, a steering knob (149) attaches to the distal portion (142) of the threaded rotator (140) that is outside of the outer/middle handle shafts (100, 110). In some embodiments, the proximal end (146) of the threaded rotator (140) is disposed next to a compression tube mount (150). In some embodiments, the threaded rotator (140) has a longitudinal lumen (141) configured to receive a catheter shaft (12).

FIG. 3A illustrates a compression tube mount (150) is positioned proximal to the threaded rotator (140). In some embodiments, the compression tube mount (150) has an elongated hollow body with an axial lumen (156) extending from one end (152) to the other end (154). The distal end (152) of the compression tube mount (150) butts against the proximal end (146) of the threaded rotator (140). In some embodiment, the threaded rotator (140) and the compression tube (150) are configured to move laterally together, while the threaded rotator (140) rotates independently from the compression tube mount (150). According to one embodiment of the present teaching, as the threaded rotator (140) rotates against the thread follower (122), the threaded rotator (140) also moves laterally, and the compression tube mount (150) moves laterally along with the threaded rotator (140). In some embodiment, such threaded rotator (140) and compression tube (150) assembly configuration can be achieved by many means known to those skilled in the art. For example, a first end cap could be used to stop proximal motion of the threaded proximal portion (144) of the threaded rotator (140), and a second end cap could be used to stop distal motion of the proximal end (154) of the compression tube mount (150).

Continue referring to FIG. 3A, the compression tube mount (150) has a key slot (158) extending from its axial lumen (156) radially away to the exterior surface. The key slot (158) is configured to receive a key on the catheter shaft (12). Through this key slot-key assembly, the catheter shaft (12) is bonded to the compression tube mount (150). Such bonding assembly prevents the catheter shaft (12) from rotating and moving laterally relative to the compression tube mount (150). In some embodiments, key slot-key assembly allows the lateral movement of the threaded rotator (140) and compression tube (150) assembly being translated to the catheter shaft (12).

FIG. 3A further illustrates a pull wire mount (160) placed proximally to the compression tube mount (150). Similar to the compression tube mount (150), the pull wire mount (160) also has an elongated hollow body with an axial lumen (166) extending from one end (162) to the other end (164). The catheter shaft (12) is slidably disposed within the axial lumen (166) of the pull wire mount (160). As shown in FIG. 3A, the pull wire mount (160) also has a key slot (168) extending from its axial lumen (166) radially away to the exterior surface. The key slot (168) is configured to receive the proximal end of the pull wire (16). In some embodiment, the proximal end of the pull wire (16) is bonded to the key slot (168) of the pull wire mount (160). According to some embodiment, the pull wire mount (160) is fixed to the middle handle shaft (110) so that the pull wire mount (160) is prevented from rotating and moving laterally relative to the middle handle shaft (110).

Now referring to FIG. 3B, the catheter shaft (12) extends proximally through the axial lumen (141) of the threaded rotator (140), the axial lumen (156) the compression tube mount (150), the axial lumen (166) of the pull wire mount (160), and then further extends proximally beyond the outer handle shaft (100), thus outside of the control handle assembly (14). According to one embodiment of the present teachings, the proximal end of the shaft is used to insert a medical implant, or as the entrance for a RF wire.

Continue referring FIG. 3B, as described above, the catheter shaft (12) bonds to the compression tube mount (150) with the key on the catheter shaft (12) disposed within the key slot (158) of the compression tube mount (150). The proximal end of the pull wire (16) bonds to the pull wire mount (160). The threaded rotator (140) joins the compression tube mount (150), together they are position distal to the pull wire mount (160). As shown in FIG. 3B, the pull wire mount (160) is proximal to the compression tube mount (150), and the threaded rotator (140) is distal to the compression tube mount (150) with the threaded proximal portion (144) next to the compression tube mount (150) and the unthreaded distal portion (142) outside of the outer handle shaft (100).

Continue referring to FIG. 3B, the pull wire mount (160), the compression tube mount (150) and the threaded rotator (140) assembly are placed inside the center lumen (116) of the middle handle shaft (110). As shown in FIG. 3B, the pull wire mount (160) is fixed to a location inside the middle handle shaft (110). The compression tube mount (150) joins to the threaded rotator (140) forming an assembly which moves distally or proximally. Such laterally movement is translated to the catheter shaft (12) through the bonding between the catheter shaft (12) and the compression tube mount (150). The movement of the compression tube mount (150) and the threaded proximal portion (144) of threaded rotator (140) assembly is limited inside the middle handle shaft (110). Although the threaded rotator (140) and compression tube assembly is configured to slide within the center lumen of the middle handle shaft (110), and thereby pulling or pushing the catheter shaft distally or proximally. The unthreaded distal portion (142) of the threaded rotator (140) extends distally outside of the middle handle shaft (110). A steering knob (149) attaches to the distal portion (142) of the threaded rotator (140). The steering knob (149) can be used by a clinical control to push, pull, and rotate the thread rotator.

Figure 3C:
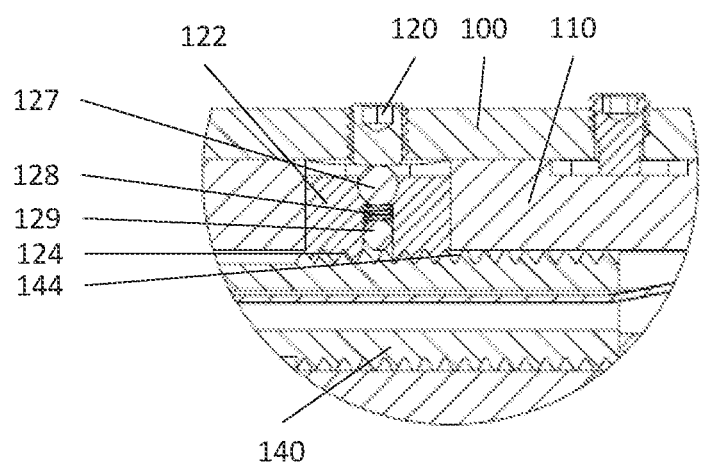

Further referring to FIG. 3C, the thread follower (122) is placed inside the thread follower retainer slot (118) on the middle handle shaft (110) with the bottom threads (124) facing the threads (144) of the threaded rotator (140). A set screw (120) is place inside the through hole (108) on the outer handle shaft (100). As illustrated in FIG. 3C, the set screw (120) slightly protrudes beyond the interior slotted surface of the outer handle shaft (100). FIG. 3C illustrates the thread follower (122) centers under the set screw (120). As shown in FIG. 3C, the set screw (120) presses on the first ball bearing (127), the first ball bearing (127) then compresses the spring (128), the spring (128) then forces the second bear bearing (129) against the bottom of the hole. The thread follower (122) then engages toward the threaded rotator (140). Threads (124) thereby engages the threads (144) of the threaded rotator (140).

Figure 3D:
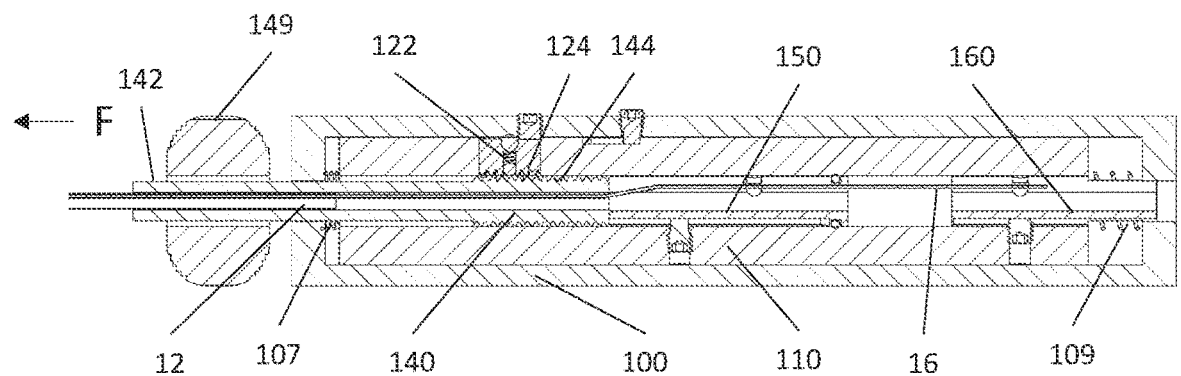

Referring again to FIG. 3B, the middle handle shaft (110), with all the assembly inside its center lumen (116), is disposed inside the center lumen (106) of the outer handle shaft (100). Two springs (107, 109), including a proximal spring (109) and a distal spring (107), are placed at each end of the middle handle shaft (110). These two springs (107, 109), at their relaxed state, force the middle handle shaft (110) inside the outer handle shaft (100) to its first position where the thread follower (122) centers under the set screw (120) thereby allowing the threads (124) of the thread follower (122) engages the threads (144) of the threaded rotator (140) as described above and illustrated in FIG. 3C. When the middle handle shaft (110) is being pulled distally with a force "F", the distal spring is compressed, the first ball bearing (127) is freed from the set screw (120). As the first ball bearing enters the longitudinal slot (105) on the interior surface (103) of the outer handle shaft (100), the spring (108) relaxed, and the thread follower (122) then moves away from the thread rotator (140). Engagement between threads (124, 144) is then released, and the middle handle shaft (110) is now in its second position where the thread rotator (140) and the compression tube mount (150) assembly moves distally and proximally with lateral force without the constriction of the threads (124, 144) engagement, as illustrated in FIG. 3D. Once the pulling force "F" is released, the proximal spring recovers and pushes the middle handle assembly back to its first position as illustrated in FIG. 3B.

Figure 4A:
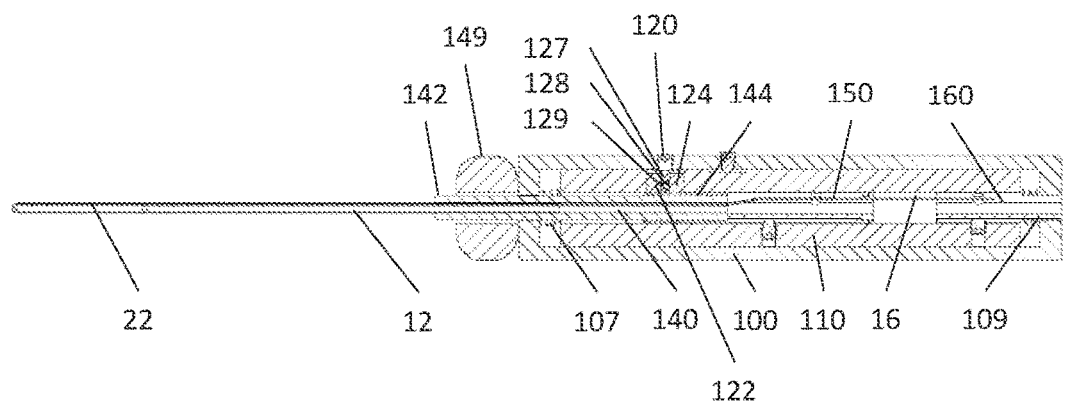
FIGS. 4A-4D are perspective views of a delivery catheter assembly including a control handle assembly and a catheter shaft with a deflectable distal portion at various operating stage, according to one embodiment of the present teaching.
Figure 4B:
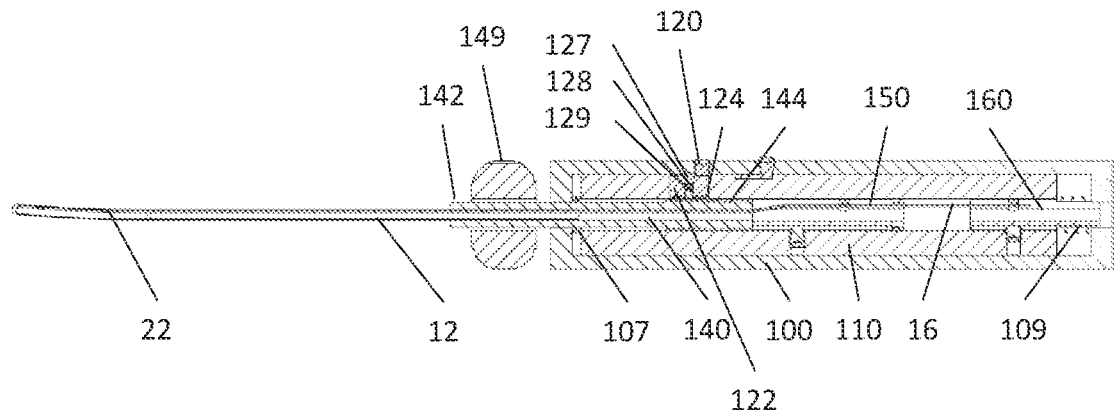
Figure 4C:
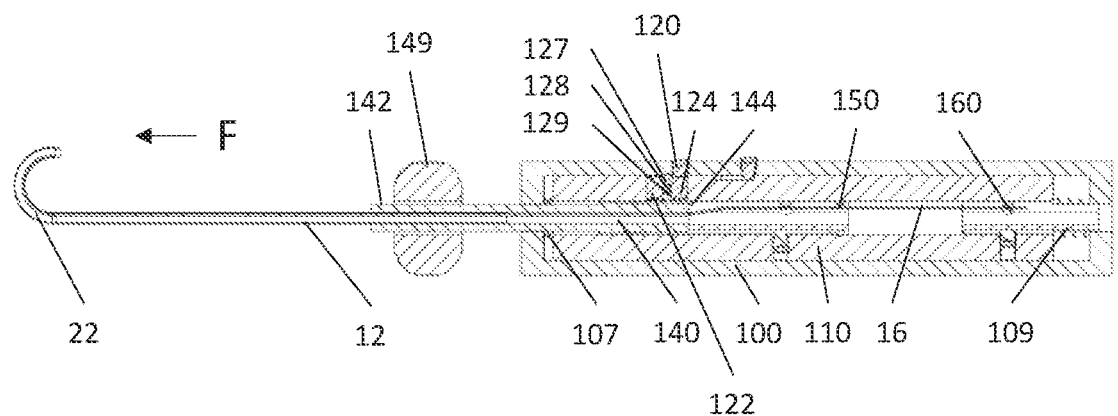
Figure 4D:
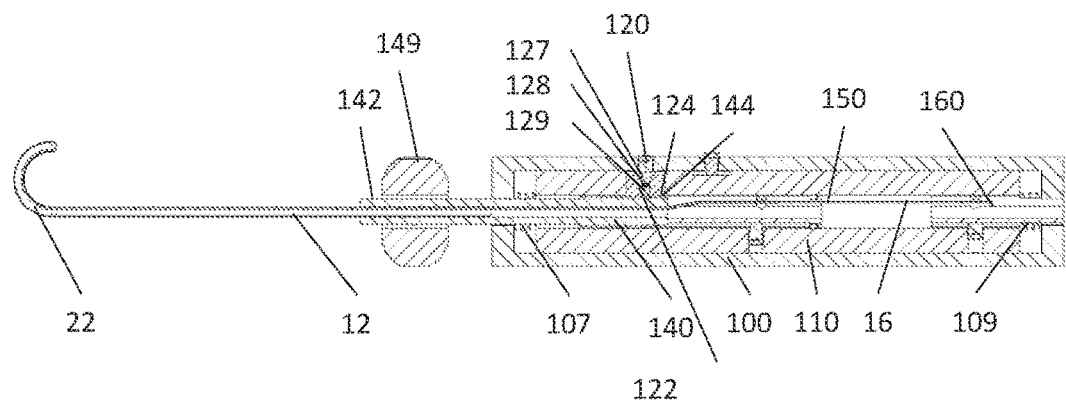

FIGS. 4A-4E illustrate the moving mechanism of the control handle assembly (14) in FIGS. 3A-3C. As shown in FIG. 4A, the middle handle shaft (110) is at its first position within the outer handle shaft (100) and the springs (107, 109) are in their relaxed state. In operation, the clinician holds the outer handle shaft (100) steady, and pulling steering knob (149) distally. As illustrated in FIG. 4B, the first ball bearing (127) is released from the set screw (120), the spring (128) recovers to its relaxed state, the threads (124, 144) disengage from each other, the thread follower (122) floats, and the middle handle shaft (110) is now in its second position. While keep holding the outer handle shaft (100) steady, the clinician can continue pull the steering knob (149) distally, the threaded rotator (140) and compression tube mount (150) assembly slide laterally inside the middle handle shaft (110), as illustrated in FIG. 4C, and carrying catheter shaft (12) with it. The distal portion (22) of the catheter shaft (12) deflects as the distance between the pull wire mount (160) and compression tube mount (150) changes. Thus such push-pull of the steering knob (149) leads to a gross displacement of the distal portion (22) of the catheter shaft (12).

As the clinician releases the outer handle shaft (100), the springs (107, 109) recover and the middle handle shaft (110) resumes its first position within the outer handle shaft (12). The set screw (120) employs the first ball bearing (127), and the thread follower (122) engages the threaded rotator (140) as illustrated FIG. 4D. According to some embodiments, the threads engagement functions as a linear actuator and converts the rotational motion of the threads into a linear motion. At this point, the clinician rotates the threaded rotator (140), and such rotation motion is translated into a lateral movement by the threads (124, 144) engagement, thereby allows the threaded rotator (140) and compression tube mount (150) assembly move laterally relative to the pull wire mount (160), as shown in FIG. 4E. Thus, such thread rotation-to-linear actuation leads to a precision displacement of the distal portion (22) of the catheter shaft (12).

In one embodiment of the present teaching, as the threaded rotator (140) rotates 180°, the distal end (24) of the catheter shaft (12) displaces of 0.5 mm to 5 mm. In some embodiments, the precision displacement of the distal portion (22) of the catheter shaft (12) depends on the step angle and pitch of the threads (124, 144) assembly. According to some embodiments, the thread (144) could have multiple starts, multiple pitches.

One skilled in the art should understand that, according to some embodiments, the design principle of the present teachings includes a quick linear motion by the control handle assembly to allow a gross displacement of the deflectable distal portion of the catheter shaft, and an automatic engagement of the thread mechanism allowing a rotation-to-linear actuation imparts a precision displacement of the deflectable distal portion of the catheter shaft. The exemplary embodiments shown in FIGS. 3A-3D incorporate such principle. The exemplary embodiments shown in FIGS. 4A-4D explains the working mechanism of such principle. One skilled in the art should understand that other design example could also be incorporate to embody such principle.

Figure 5A:
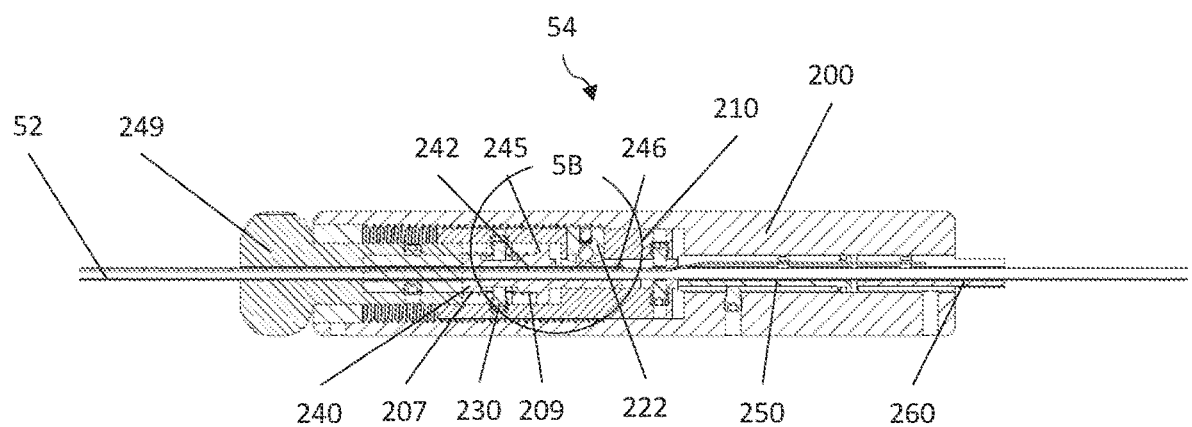
FIGS. 5A-5E are perspective views of a control handle assembly at various operating stage, according to one embodiment of the present teaching.
Figure 5B:
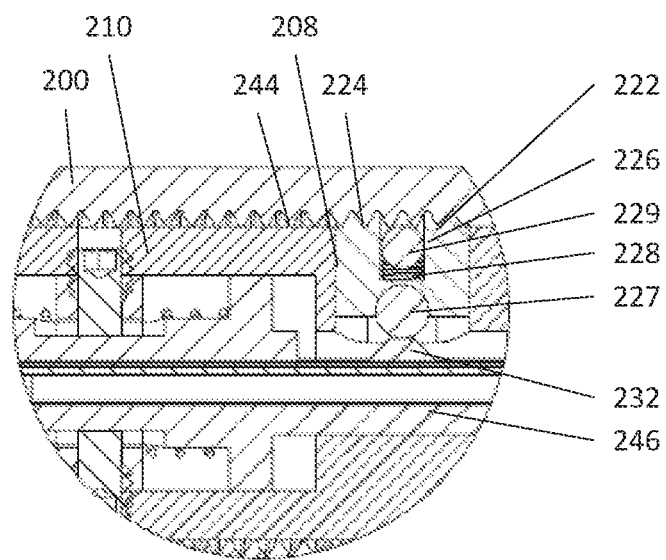
Figure 5C:
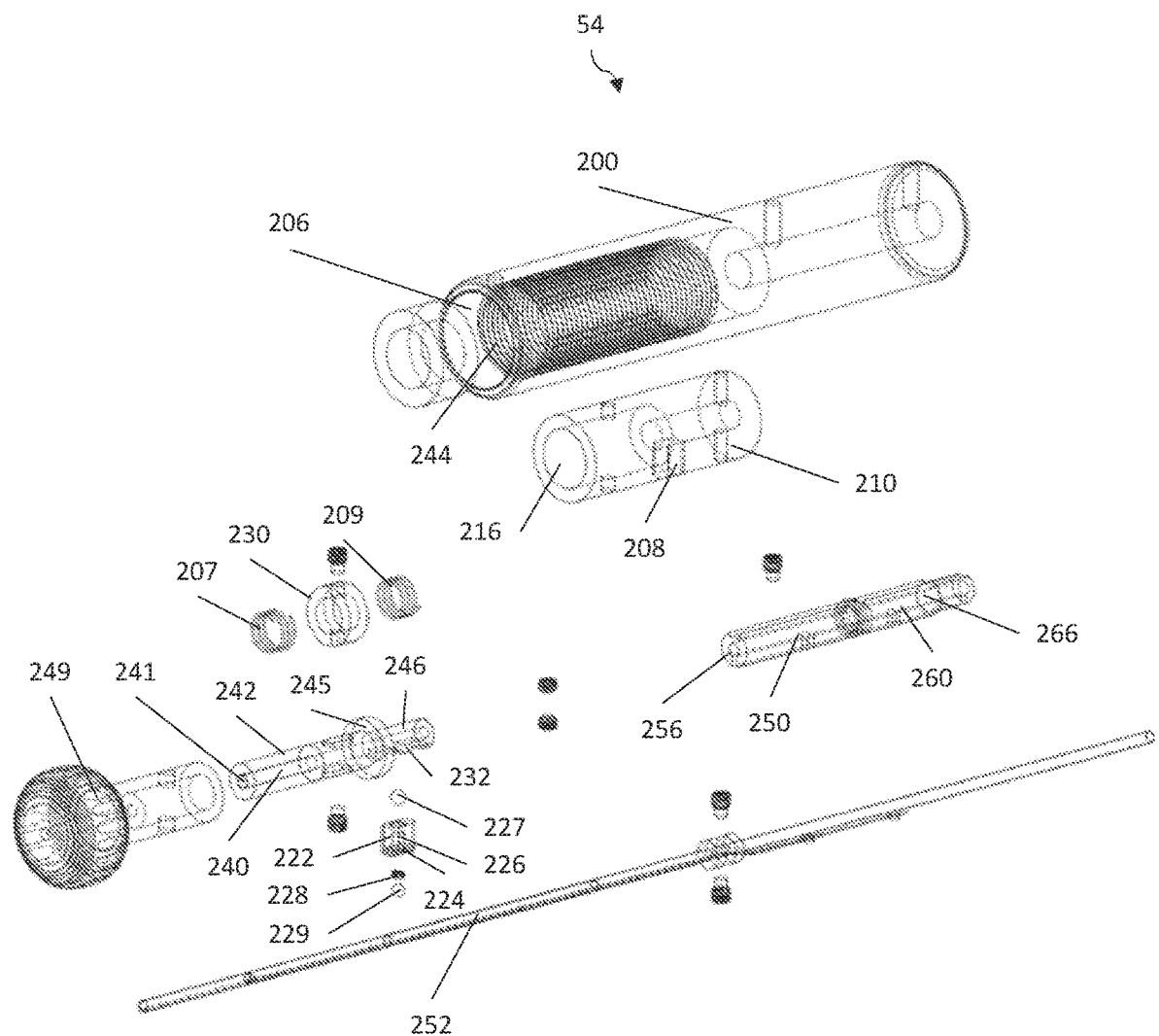

FIGS. 5A-5C further illustrate another embodiment of present teaching. In the most part, this exemplary embodiment is similar to the exemplary embodiment described above. For example, a catheter shaft (52) extends through the center lumen (241) of a rotating cam (240), the center lumen (256) of the compression tube mount (250), and the center lumen (266) of the pull wire mount (260). The catheter shaft (52) extends further proximally outside of the control handle assembly (54). The pull wire mount (260) is proximal to the compression tube mount (250), and the rotator cam (240) is distal to the compression tube mount (250). Similar to described above, catheter shaft (52) fixes to the compression tube mount (250) through a key slot-key assembly, preventing the catheter shaft (52) from rotating and moving laterally relative to the compression tube mount (250). The proximal end of the pull wire also fixes to the pull wire mount (260).

Unlike what has been described above, in this exemplary embodiment, as shown in FIG. 5C, the rotating cam (240) has an enlarged distal portion (242) and a smaller proximal portion (246) with a flange (245) dividing the two portions. A distal knob (249) joins the distal portion (242) of the rotating cam (240). The distal knob (249) also has a center lumen allowing the catheter shaft (52) to extend through. A centering bushing (230) also rides over the distal portion of the rotating cam (240) with two centering springs (207, 209) at each end of the centering bushing (230). As shown in FIG. 5B, the distal knob (249) is distal to the distal spring (207), and the distal spring (207) is distal to the centering bushing (230), and the centering bushing (230) is distal to the proximal spring (209). According to one embodiment, the centering bushing (230) fixes to the distal portion (242) of the rotating cam (240) in such way that the centering bushing (230) is prevented from rotating relative to the rotating cam (240), while allowed to move longitudinally relative to the rotating cam (240).

Further referring to FIG. 5B, unlike exemplary embodiment described in reference to FIGS. 3A-3D, the rotating cam (240) has no threads. Instead, a thread follower (222) positions over a ridge (232) on proximal portion (246) of the rotating cam (240). Similar to what has been described in reference to FIG. 3B, a hole (226) housing a second ball bearing (229) inside and a spring (228) trapped in between of a first ball bearing (227) and the second ball bearing (229). The thread follower (222) also has a thread facing radially away from the rotating cam (240). The threads (224) on the thread follower (222) is configured to engage the threads (244) on the interior surface of the outer handle shaft (200) as described below.

FIG. 5C, further illustrates a middle handle shaft (210) has a center lumen (216) configured to house the rotating cam (240). The middle handle shaft (210) has a through hole (208) extends from its center lumen to its exterior surface, configured to house the thread follower (222). As shown in FIG. 5A, the middle handle shaft (210) joins the compression tube mount (250) at its proximal portion. According to one embodiment of the present teaching, the compression tube mount (250) joins the middle handle shaft (210) in such way that allows the middle handle shaft (210) rotate independently from the compression tube mount (250), while prevent the middle handle shaft (210) from move laterally relative to the compression tube mount (250).

Further referring to FIG. 5A, the outer handle shaft (200) has a center lumen (206) configured to house the pull wire mount (260), the compression tube mount (250) and the middle handle shaft (210) carrying rotating cam (240) and the distal knob (249). The pull wire mount fixes to the outer handle shaft (200), and the distal knob (249) extends distally outside of the center lumen (206) of the distal knob (249).

FIG. 5A illustrates one embodiment of the present teaching where the middle handle shaft (210) is in its first position. As shown in the figure, centering springs (207, 209) are relaxed, the first ball bearing (227) centers over the ridge (232) on the proximal portion (246) of the rotating cam (240). As such, the first ball bearing compresses the spring (228) and the second ball bearing (229), the thread follower (222) thereby forced toward the interior surface of the outer handle shaft (200). Threads (224, 244) then engage each other. At this point, by holding knob (249) steady, a clinician can then rotates the outer handle shaft (200). Since the rotating cam (240) joins the middle handle shaft (210), and the middle handle shaft (210) joins the compression tube mount (250), the threads (224, 244) rotation allows the middle handle shaft (210) and compression tube mount (250) assembly move laterally relative to the pull wire mount (260). Thus, such thread rotation-to-linear actuation leads to a precision displacement of the distal portion (52) of the catheter shaft (52).

Figure 5D:
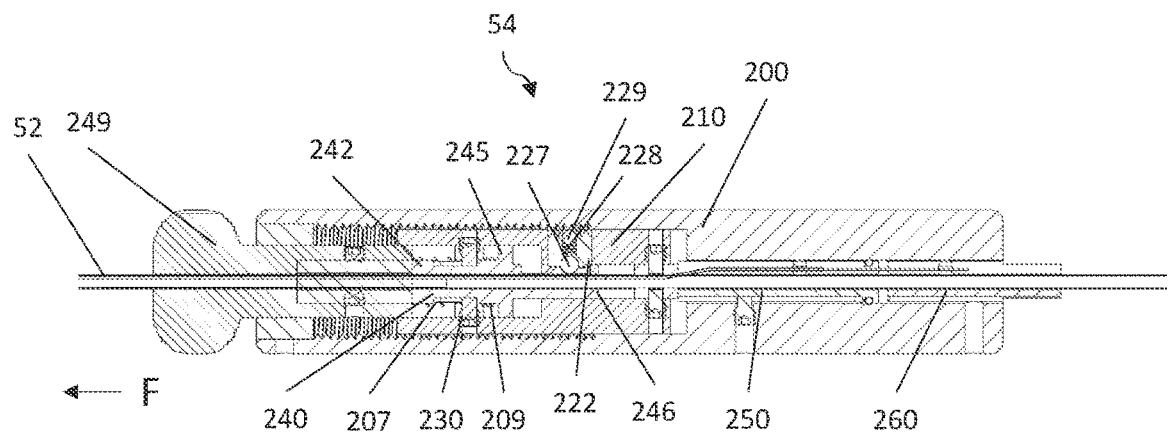
Figure 5E:
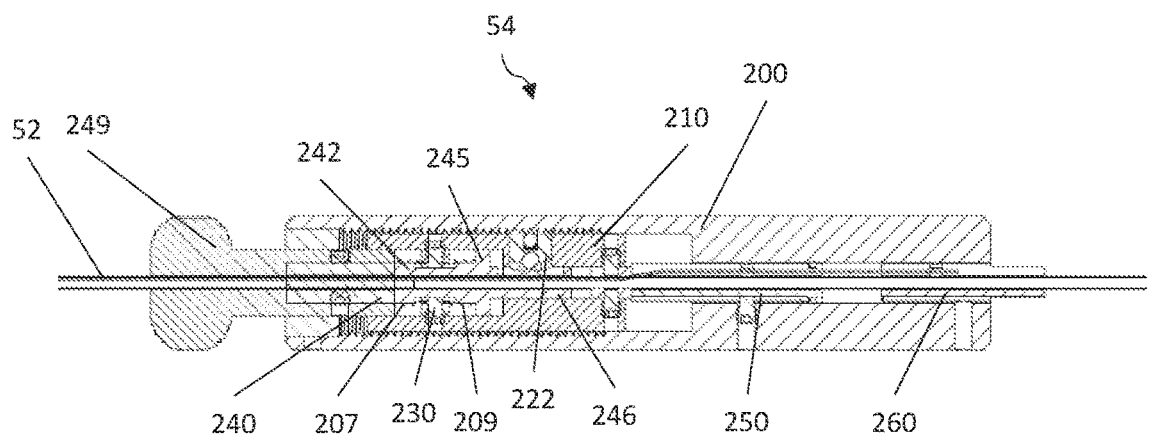

FIG. 5D illustrates one embodiment of the present teaching where the middle handle shaft (210) is in its second position. As shown in the figure, as the knob (249) being pulled distally, the proximal spring (209) compresses, and the rotating cam (240) being pulled distally. The ridge (232) on the proximal portion (246) of the rotating cam (240) moves distally relative to the first ball bearing (227). FIG. 5D shows that first ball bearing free from the ridge (232), the spring (228) in between the two ball bearing (227, 229) relaxes. Such relaxation carries the thread follower (222) moving away from the interior thread of the outer handle shaft (200). Threads (224, 244) then disengage each other. At this point, by holding outer handle shaft (200) steady, a clinician call can push the knob (249) distally, thereby changing the distance between the pull wire mount (260) and compression tube mount (250) and leading the distal portion (52) of the catheter shaft (52) deflect. Thus such push-pull of the knob (249) leads to a gross displacement of the distal portion (52) of the catheter shaft (52).

As the clinician releases the outer handle shaft (100), the springs (107, 109) recover and the middle handle shaft (110) resumes its first position within the outer handle shaft (12). The set screw (120) employs the first ball bearing (127), and the thread follower (122) engages the threaded rotator (140) as illustrated FIG. 4D. According to some embodiments, the threads engagement functions as a linear actuator and converts the rotational motion of the threads into a linear motion. At this point, the clinician rotates the threaded rotator (140), and such rotation motion is translated into a lateral movement by the threads (124, 144) engagement, thereby allows the threaded rotator (140) and compression tube mount (150) assembly move laterally relative to the pull wire mount (160), as shown in FIG. 4E. Thus, such thread rotation-to-linear actuation leads to a precision displacement of the distal portion (22) of the catheter shaft (12).

As the clinician releases the force applied to the knob (249), the spring (209) recovers and the middle handle shaft (210) resumes its first position within the outer handle shaft (200). The thread follower (222) repositions over a ridge (232) on proximal portion (246) of the rotating cam (240). The spring (228) compressed and the threads (224, 244) engage each other as illustrated FIG. 5D. According to some embodiments, the threads engagement functions as a linear actuator and converts the rotational motion of the threads into a linear motion. At this point, the clinician rotates the rotating cam (240), and such rotation motion is translated into a lateral movement by the threads (224, 244) engagement, thereby allows the compression tube mount (250) move laterally relative to the pull wire mount (260). Thus, such thread rotation-to-linear actuation leads to a precision displacement of the distal portion of the catheter shaft (52).

According to some embodiments, although exemplary embodiment has been described above in order to explain the present invention, one skilled in the art should understand, design details could be replaced to achieve the same function. For example, set screw (120) described in reference to FIGS. 3A-3D could be place with a ridge design. Proximal and distal springs (107, 109, 207, and 209) could have different size, shape, and recover force. Such design variation should be considered as within the scope of present invention.

Exemplary embodiment shown in FIG. 5A-5D also accomplishes the above described design principle of the present teaching. That is, a quick linear motion by the control handle assembly to allow a gross displacement of the deflectable distal portion of the catheter shaft, and an automatic engagement of the thread mechanism allowing a rotation-to-linear actuation imparts a precision displacement of the deflectable distal portion of the catheter shaft. Thus, those skilled in the art should understand that the exemplary embodiments described above could be modified in various execution while still achieve the same design principle.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

The invention claimed is:
1. An apparatus, comprising:
a catheter;
a handle shaft, disposed at a proximal end of the catheter;
a wire, extending from a distal part of the catheter, proximally through the catheter to the handle shaft;
a knob, disposed outside of the handle shaft; and
a thread mechanism that provides operative coupling between the knob and the handle shaft such that:
rotation of the knob with respect to the handle shaft alters tension in the wire via the thread mechanism functioning as a linear actuator, and non-rotational axial movement of the knob with respect to the handle shaft alters tension in the wire without the thread mechanism functioning as a linear actuator.

2. The apparatus according to claim 1, wherein the wire is coupled to the catheter such that increasing tension in the wire deflects a distal portion of the catheter.

3. The apparatus according to claim 1, wherein the thread mechanism:
    comprises a first thread coupled to the knob, and a second thread coupled to the handle and threadedly engaged with the first thread, and
    functions as the linear actuator by the first thread threadedly moving along the second thread in response to the rotation of the knob with respect to the handle shaft.

4. The apparatus according to claim 3, wherein the first thread circumscribes a central longitudinal axis, and the second thread is disposed laterally from the first thread.

5. The apparatus according to claim 3, wherein the first thread is fixedly coupled to the knob.

6. The apparatus according to claim 3, wherein the thread mechanism facilitates the non-rotational axial movement of the knob with respect to the handle shaft by the second thread floating axially alongside the first thread upon application to the knob of a non-rotational axial force.

7. The apparatus according to claim 6, further comprises a spring that facilitates the floating of the first thread axially alongside the second thread by, in response to the non-rotational axial movement of the knob with respect to the handle shaft, pushing the second thread laterally away from the first thread.

8. The apparatus according to claim 7, further comprising a ball bearing, disposed between the spring and the first thread, wherein the spring is configured to, in response to the non-rotational axial movement of the knob with respect to the handle shaft, push the second thread laterally away from the first thread by pushing the ball bearing against the first thread.

9. The apparatus according to claim 1, wherein the operative coupling provided by the thread mechanism is such that:
    non-rotational axial movement, in a first axial direction, of the knob with respect to the handle shaft increases tension in the wire without the thread mechanism functioning as a linear actuator; and
    non-rotational axial movement, in a second axial direction, of the knob with respect to the handle shaft reduces tension in the wire without the thread mechanism functioning as a linear actuator, the second axial direction being opposite to the first axial direction.

10. The apparatus according to claim 9, wherein the operative coupling provided by the thread mechanism is such that:
    rotation, in a first rotational direction, of the knob with respect to the handle shaft increases tension in the wire via the thread mechanism functioning as a linear actuator, and
    rotation, in a second rotational direction, of the knob with respect to the handle shaft reduces tension in the wire via the thread mechanism functioning as a linear actuator, the second rotational direction being opposite to the first rotational direction.

11. The apparatus according to claim 1, wherein the thread mechanism allows the non-rotational axial movement of the knob with respect to the handle shaft by transiently disengaging upon application to the knob of a non-rotational axial force.

12. The apparatus according to claim 11, wherein:
    the non-rotational axial movement of the knob with respect to the handle shaft is non-rotational axial movement of the knob in a first axial direction with respect to the handle shaft,
    the non-rotational axial force is in the first axial direction with respect to the handle, and
    the thread mechanism allows the non-rotational axial movement of the knob in the first axial direction with respect to the handle shaft by transiently disengaging upon application, to the knob, of the non-rotational axial force in the first axial direction with respect to the handle.

13. The apparatus according to claim 1, wherein the knob is collinear with the handle shaft.

14. The apparatus according to claim 1, wherein the catheter defines a lumen adapted to allow an implant to slide therethrough.

15. The apparatus according to claim 1, wherein a distal end of the catheter is disposed distally from the handle shaft, and a proximal end of the catheter is disposed proximally from the handle shaft.

* * * * *